US011666685B2

(12) United States Patent
Lai et al.

(10) Patent No.: US 11,666,685 B2
(45) Date of Patent: Jun. 6, 2023

(54) BIOMATERIAL AND METHOD FOR PROMOTING TISSUE REGENERATION BY USING THE BIOMATERIAL

(71) Applicant: WIZDOM INC., Las Vegas, NV (US)

(72) Inventors: Yi-Chung Lai, Las Vegas, NV (US); Wen-Yi Chen, Las Vegas, NV (US); Yung-Lung Liu, Las Vegas, NV (US)

(73) Assignee: WIZDOM INC., Las Vegas, NV (US)

( * ) Notice: Subject to any disclaimer, the term of this patent is extended or adjusted under 35 U.S.C. 154(b) by 46 days.

(21) Appl. No.: 16/991,498

(22) Filed: Aug. 12, 2020

(65) Prior Publication Data

US 2021/0290826 A1    Sep. 23, 2021

(30) Foreign Application Priority Data

Mar. 18, 2020   (TW) .................. 109109048

(51) Int. Cl.
| | | |
|---|---|---|
| *A61K 31/64* | (2006.01) | |
| *A61K 47/36* | (2006.01) | |
| *A61L 27/20* | (2006.01) | |
| *A61P 3/10* | (2006.01) | |
| *A61L 27/54* | (2006.01) | |
| *A61L 27/22* | (2006.01) | |
| *A61L 27/24* | (2006.01) | |
| *A61K 31/155* | (2006.01) | |
| *A61K 31/165* | (2006.01) | |
| *A61K 31/4439* | (2006.01) | |
| *A61K 31/702* | (2006.01) | |
| *A61K 31/445* | (2006.01) | |
| *A61K 31/136* | (2006.01) | |
| *A61K 31/4985* | (2006.01) | |
| *A61K 31/403* | (2006.01) | |
| *A61K 31/40* | (2006.01) | |
| *A61K 31/522* | (2006.01) | |
| *A61K 31/7004* | (2006.01) | |
| *A61K 31/7042* | (2006.01) | |
| *A61K 47/42* | (2017.01) | |
| *A61K 47/02* | (2006.01) | |
| *A61L 27/12* | (2006.01) | |

(52) U.S. Cl.
CPC ............ *A61L 27/54* (2013.01); *A61K 31/136* (2013.01); *A61K 31/155* (2013.01); *A61K 31/165* (2013.01); *A61K 31/40* (2013.01); *A61K 31/403* (2013.01); *A61K 31/445* (2013.01); *A61K 31/4439* (2013.01); *A61K 31/4985* (2013.01); *A61K 31/522* (2013.01); *A61K 31/64* (2013.01); *A61K 31/702* (2013.01); *A61K 31/7004* (2013.01); *A61K 31/7042* (2013.01); *A61K 47/02* (2013.01); *A61K 47/36* (2013.01); *A61K 47/42* (2013.01); *A61L 27/12* (2013.01); *A61L 27/20* (2013.01); *A61L 27/222* (2013.01); *A61L 27/24* (2013.01); *A61L 2300/204* (2013.01); *A61L 2300/206* (2013.01); *A61L 2300/21* (2013.01); *A61L 2300/216* (2013.01); *A61L 2300/232* (2013.01); *A61L 2430/02* (2013.01)

(58) Field of Classification Search
CPC ...... A61P 3/10; A61P 9/00; A61P 3/00; A61K 2300/00; A61K 31/728; A61K 8/65; A61K 31/722; A61K 31/734; A61K 47/42; A61K 31/715; A61K 9/0024; A61K 31/00; A61K 9/7007; A61K 38/28; A61L 27/20; A61L 2430/34; A61L 26/0023; A61L 27/24; A61L 2430/02; A61L 2300/412

See application file for complete search history.

(56) References Cited

U.S. PATENT DOCUMENTS

| | | | | |
|---|---|---|---|---|
| 2002/0141967 A1* | 10/2002 | Williams | ................ | A61L 27/18 |
| | | | | 424/78.37 |
| 2003/0114936 A1* | 6/2003 | Sherwood | ............. | B29C 64/165 |
| | | | | 435/402 |
| 2012/0270810 A1* | 10/2012 | Preiss-Bloom | ......... | A61L 24/10 |
| | | | | 514/21.2 |
| 2016/0000974 A1* | 1/2016 | Arinzeh | ................ | A61L 27/365 |
| | | | | 424/426 |
| 2017/0136152 A1* | 5/2017 | Izadyar | .................. | A61K 45/06 |
| 2017/0182080 A1* | 6/2017 | Han | ...................... | A61K 31/715 |
| 2019/0031774 A1* | 1/2019 | Bujas-Bobanovic | ..... | A61P 3/10 |

FOREIGN PATENT DOCUMENTS

WO    WO-2017075530 A1 *   5/2017   ............. A61K 38/32

* cited by examiner

*Primary Examiner* — Tracy Liu

(74) *Attorney, Agent, or Firm* — Muncy, Geissler, Olds & Lowe, P.C.

(57) ABSTRACT

The present disclosure provides a biomaterial and a method for promoting tissue regeneration by using the biomaterial.

13 Claims, 3 Drawing Sheets

Specification includes a Sequence Listing.

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
gagaagccgg gacacagttc                                              20

<210> SEQ ID NO 2
<211> LENGTH: 21
<212> TYPE: DNA
<213> ORGANISM: Artificial Sequence
<220> FEATURE:
<223> OTHER INFORMATION: synthetic primer

<400> SEQUENCE: 2
cctcctcaac tgggatgatg c                                            21

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
```
taggcgcatt tcaggtgctt                                                    20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
ggtgtggtag tgagtggtgg                                                    20

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
taggactgta ggaccggagc                                                    20

<210> SEQ ID NO 6
<211> LENGTH: 22
<212> TYPE: DNA
<213> ORGANISM: Artificial Sequence
<220> FEATURE:
<223> OTHER INFORMATION: synthetic primer

<400> SEQUENCE: 6
catagtgaac ttcctcctgg gg                                                 22

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
attgacgggt acctctccca                                                    20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
gaaaaagcgg gtggtgcaat                                                    20

<210> SEQ ID NO 9
<211> LENGTH: 21
<212> TYPE: DNA
<213> ORGANISM: Artificial Sequence
<220> FEATURE:
<223> OTHER INFORMATION: synthetic primer

<400> SEQUENCE: 9
ctcacactcc tcgccctatt g                                                  21

<210> SEQ ID NO 10
<211> LENGTH: 21
<212> TYPE: DNA
<213> ORGANISM: Artificial Sequence

```
<220> FEATURE:
<223> OTHER INFORMATION: synthetic primer

<400> SEQUENCE: 10
gcttggacac aaaggctgca c                                             21

<210> SEQ ID NO 11
<211> LENGTH: 17
<212> TYPE: DNA
<213> ORGANISM: Artificial Sequence
<220> FEATURE:
<223> OTHER INFORMATION: synthetic primer

<400> SEQUENCE: 11
agaggtcgcc ctggagc                                                  17

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
caggaacacc ctgttcacca                                               20

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
aatgggcagc cgttaggaaa                                               20

<210> SEQ ID NO 14
<211> LENGTH: 22
<212> TYPE: DNA
<213> ORGANISM: Artificial Sequence
<220> FEATURE:
<223> OTHER INFORMATION: synthetic primer

<400> SEQUENCE: 14
gcccaatacg accaaatcag ag                                            22
```

BIOMATERIAL AND METHOD FOR PROMOTING TISSUE REGENERATION BY USING THE BIOMATERIAL

CROSS-REFERENCE TO RELATED APPLICATION

This application claims priority of Taiwan patent application No. 109109048, filed on Mar. 18, 2020, the content of which is incorporated herein in its entirety by reference.

BACKGROUND OF THE INVENTION

1. Field of the Invention

The present invention relates to a biomaterial and a method for promoting tissue regeneration by using the biomaterial.

2. The Prior Art

Tissue engineering is a new discipline that combines cell biology and material science to construct tissues or organs in vitro or in vivo. The core of tissue engineering is to build a three-dimensional complex of cells and biomaterials, which are used to reconstruct shape the defective tissues in three aspects: morphology, structure and function, and to achieve permanent replacement. Bone tissue engineering refers to planting the isolated autologous osteoblasts, bone marrow stromal cells, or chondrocytes with high concentration after in vitro culture and expansion on a cell scaffold or an extracellular matrix, and implanting this kind of cell hybrid material into the bone defect site. While the biomaterial is gradually degraded, the planted osteoblasts continue to proliferate, thereby achieving the purpose of repairing bone tissue defects.

The materials used for repairing bone defect are mainly bio-inorganic materials and organic polymer materials. Among organic polymer materials, poly (lactic-co-glycolic acid)(PLGA), which is formed by random polymerization of lactic acid and glycolic acid, has been widely studied. It has advantages of good biocompatibility, biodegradability, and adjustability of degradation rate. In addition, PLGA is degraded into lactic acid and glycolic acid by ester bond hydrolysis, and finally degraded into carbon dioxide and water to be excreted out of the body.

The prior art mainly uses heating technology to shape the stent. This high-temperature application would denature some protein drugs and limit the types of drug carriers. Because there are fewer large-scale heating devices, the choice of heating technology also limits the stent preparation. Although there have been some studies on microsphere drug-loaded stents, microcapsule stents are still rarely reported, and drug carriers in the microcapsule stents are even more so. In addition, the methods used to promote regeneration of bone tissues in the prior art often have the disadvantages of poor biocompatibility and poor effects.

In order to solve the above problems, those skilled in the art urgently need to develop a novel method for promoting tissue regeneration (such as regeneration of bone tissues) for the benefit of a large group of people in need thereof.

SUMMARY OF THE INVENTION

A primary objective of the present invention is to provide a biomaterial for promoting regeneration of bone tissues, comprising a biocompatible polymer, an inorganic salt, and a hypoglycemic drug.

According to an embodiment of the present invention, the hypoglycemic drug is selected from the group consisting of: biguanide, insulin, sulfonylurea, meglitinide, thiazolidinedione, an α-Glucosidase inhibitor, a dipeptidyl peptidase 4 (DPP-4) inhibitor, a sodium-glucose transport protein 2 (SGLT2) inhibitor, and cycloset.

According to an embodiment of the present invention, the biguanide is metformin.

According to an embodiment of the present invention, the sulfonylurea is selected from the group consisting of: glipizide, glyburide, gliclazide, and glimepiride.

According to an embodiment of the present invention, the meglitinide is a repaglinide or a nateglinide.

According to an embodiment of the present invention, the Thiazolidinedione is a rosiglitazone or a pioglitazone.

According to an embodiment of the present invention, the α-Glucosidase inhibitor is selected from the group consisting of: acarbose, miglitol, and voglibose.

According to an embodiment of the present invention, the DPP-4 inhibitor is selected from the group consisting of: sitagliptin, saxagliptin, vildagliptin, linagliptin, and alogliptin.

According to an embodiment of the present invention, the SGLT2 inhibitor is a dapagliflozin or a canagliflozin.

According to an embodiment of the present invention, the cycloset is a bromocriptine.

According to an embodiment of the present invention, the biomaterial further comprises a binder, wherein the binder is a cross-linking agent.

According to an embodiment of the present invention, the biocompatible polymer has a concentration of 1-50% (w/v), the inorganic salt has a concentration of 1-50% (w/v), the hypoglycemic drug has a concentration of 1 nM-1 M, and the binder has a concentration of 1-50 wt %.

According to an embodiment of the present invention, the biocompatible polymer is a polysaccharide, a protein, or a combination thereof.

According to an embodiment of the present invention, the polysaccharide is selected from the group consisting of: hyaluronic acid, alginate, chitosan, and any combination thereof.

According to an embodiment of the present invention, the protein is a gelatin, a collagen, or a combination thereof.

According to an embodiment of the present invention, the inorganic salt is selected from the group consisting of: hydroxylapatite (Hap), tricalcium phosphate (TCP), dicalcium phosphate (DCP), dicalcium phosphate dihydrate (DCPD), tetracalcium phosphate (TTCP), carbonate, nitrate, sulfate, potassium salts, sodium salts, and magnesium salts.

According to an embodiment of the present invention, the biocompatible polymer is in a form of a colloid, a scaffold, a sphere, a powder, or a film.

According to an embodiment of the present invention, the biocompatible polymer is crosslinked by an enzyme selected from the group consisting of: transglutaminase, lipase, peptidase, sortase, oxidoreductase, tyrosinase, polyphenoloxidase (PPO), laccase, peroxidase, lysyl oxidase, and amine oxidase.

According to an embodiment of the present invention, the biocompatible polymer or the inorganic salt has an average size from 1 nm to 1 mm.

Another objective of the present invention is to provide a method for promoting tissue regeneration, comprising administering to a subject in need thereof the aforementioned biomaterial.

According to an embodiment of the present invention, the tissue regeneration is regeneration of bone tissues.

In summary, the biomaterial of the present invention has an effect on regulating osteoblast-specific genes (including alkaline phosphatase (ALPP) gene, runt-related transcription factor 2 (RUNX2) gene, osterix (SP7) gene, osteonectin (SPARC) gene, osteocalcin (BGLAP) gene, and collagen type I alpha 1 (COL1A1) gene) to promote tissue regeneration (such as regeneration of bone tissues), and human experiments are also proved effective.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
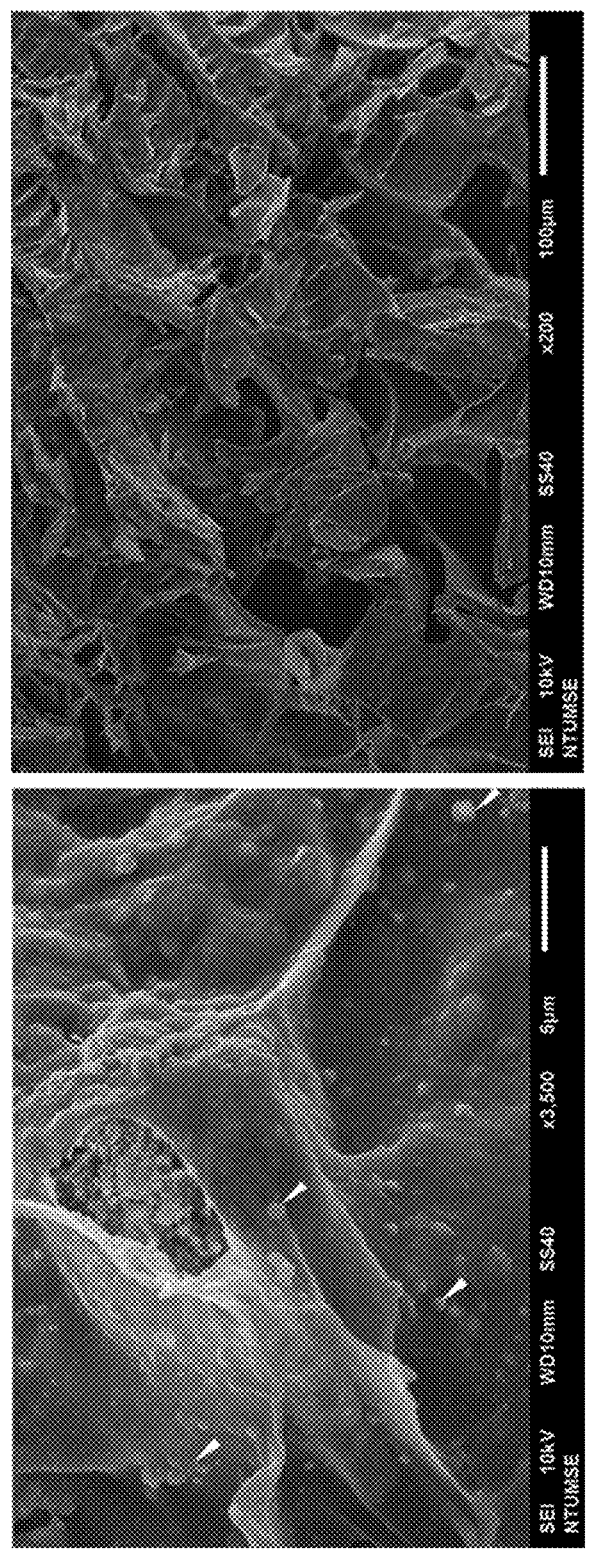
FIG. 1 is a microstructure diagram of a biomaterial of the present invention.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Unless otherwise defined, all technical and scientific terms used herein have the same meaning as commonly understood by one of ordinary skill in the art to which the present invention belongs. As used herein, the following terms have the following meanings.

Unless specified otherwise in the context, the singular forms "a", "an", and "the" described herein and in claims include plural referents. The terms such as "a", "the", "one or more", "plurality" and "at least one" are interchangeable.

The terms "comprising", "including", "containing", and "having" described herein may also be interchangeable without limitation.

In addition, the term "and/or" is used herein to specifically express one or both of two particular features or compositions. Therefore, the term "and/or" is used to express a sentence such as "A and/or B" including "A and B", "A or B", "(individual) A", and "(individual) B". Similarly, the term "and/or" is used to express a sentence such as "A, B, and/or C" which includes the meanings described below: A, B and C; A, B or C; A or C; A or B; B or C; A and C; A and B; B and C; (individual) A; (individual) B; (individual) C.

According to the present invention, the data show 4 independent experiments as mean±SD.

As used herein, "hyperglycemic drugs" refer to clinically available hypoglycemic drugs, including, but not limited to, biguanide, insulin, sulfonylurea, meglitinide, thiazolidinedione, an α-Glucosidase inhibitor, a dipeptidyl peptidase 4 (DPP-4) inhibitor, a sodium-glucose transport protein 2 (SGLT2) inhibitor, and cycloset.

According to the present invention, the biguanide is metformin; the sulfonylurea is selected from the group consisting of: glipizide, glyburide, gliclazide, and glimepiride; the meglitinide is a repaglinide or a nateglinide; the thiazolidinedione is a rosiglitazone or a pioglitazone; the α-Glucosidase inhibitor is selected from the group consisting of: acarbose, miglitol, and voglibose; the DPP-4 inhibitor is selected from the group consisting of: sitagliptin, saxagliptin, vildagliptin, linagliptin, and alogliptin; the SGLT2 inhibitor is a dapagliflozin or a canagliflozin; the cycloset is a bromocriptine.

According to the present invention, the hypoglycemic drug has a concentration of 1 nM-1 M. Preferably, the hypoglycemic drug has a concentration of 1 μM-mM. More preferably, the hypoglycemic drug has a concentration of 10 μM-100 μM.

The hypoglycemic drug referred to herein is a drug that is dissolved in a solvent. The solvent may be any polar or non-polar solvent. In a preferred embodiment, the polar solvent is water.

According to the present invention, the biomaterial can be prepared as a medicament. The medicament can be manufactured to a form suitable for parenteral, oral or topical administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, external preparation, and the like.

According to the present invention, the medicament may further comprise a pharmaceutically acceptable carrier which is widely used in pharmaceutically manufacturing techniques. For example, the pharmaceutically acceptable carrier can comprise one or more reagents selected from the group consisting of solvent, buffer, emulsifier, suspending agent, decomposer, disintegrating agent, dispersing agent, binding agent, excipient, stabilizing agent, chelating agent, diluent, gelling agent, preservative, wetting agent, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, the medicament can be administered by parenteral routes selected from the group consisting of intraepidermal injection, subcutaneous injection, intradermal injection, intramuscular injection, intravenous injection, and intralesional injection.

According to the present invention, the medicament can be manufactured to an external preparation suitable for topical application to the skin using techniques well known to those skilled in the art, including, but not limited to, emulsion, gel, ointment, cream, patch, liniment, powders, aerosol, spray, lotion, serum, paste, foam, drop, suspension, salve, and bandage.

According to the present invention, the external preparation is prepared by mixing the medicament of the present invention with a base well known to those skilled in the art.

According to the present invention, the base may comprise one or more additives selected from the group consisting of water, alcohols, glycol, hydrocarbons such as petroleum jelly and white petrolatum, wax such as paraffin and yellow wax, preserving agents, antioxidants, surfactants, absorption enhancers, stabilizing agents, gelling agents such as Carbopol® 974P, microcrystalline cellulose and carboxymethylcellulose, active agents, humectants, odor absorbers, fragrances, pH adjusting agents, chelating agents, emulsifiers, occlusive agents, emollients, thickeners, solubilizing agents, penetration enhancers, anti-irritants, colorants, and propellants. The selection and quantity of these additives fall within the scope of professional literacy and routine techniques of those skilled in the art.

Example 1

Preparation of Biomaterial and Evaluation of the Effect of Biomaterial on Regulating Osteoblast-Specific Genes In an embodiment of the present invention, a 1-50% (w/v) biocompatible polymer solution was prepared first. A protein molecule or a polysaccharide molecule may be used as the biocompatible polymer. When the biocompatible polymer is a protein molecule, a gelatin solution (Sigma-Aldrich) is preferred, wherein the gelatin is obtained from the skin of pigs (G1890 (9000-70-8), Sigma-Aldrich). It can also be replaced by collagen. When the biocompatible polymer is a polysaccharide molecule, the polysaccharide molecule can be hyaluronic acid, alginate, chitosan, or a combination thereof. In this example, the biocompatible polymer is in a form of a colloid, a scaffold, a sphere, a powder, or a film.

Next, 1-50% (w/v) hydroxyapatite (Hap, Sigma-Aldrich, 677418 (12167-74-7)) was added to the gelatin solution, and then metformin (Sigma-Aldrich) (1,1-Dimethylbiguanide hydrochloride, D150959 (1115-70-4), Sigma-Aldrich) was added to the gelatin solution, such that the metformin has a concentration of 50 µM. In this example, hydroxyapatite is an inorganic salt, which can be substituted by tricalcium phosphate (TCP), dicalcium phosphate (DCP), dicalcium phosphate dihydrate (DCPD), tetracalcium phosphate (TTCP), carbonate, nitrate, sulfate, potassium salts, sodium salts, or magnesium salts. In this example, the biocompatible polymer or the inorganic salt has an average size from 1 nm to 1 mm.

In this example, the metformin is a biguanide which is a hypoglycemic drug. Alternatively, the hypoglycemic drug is selected from the group consisting of: insulin, sulfonylurea, meglitinide, thiazolidinedione, an α-Glucosidase inhibitor, a dipeptidyl peptidase 4 (DPP-4) inhibitor, a sodium-glucose transport protein 2 (SGLT2) inhibitor, and cycloset.

1-50% wt % enzyme cross-linking agent (Ajinomoto) was added, and the resultant mixture was continuously stirred for 24 hours. Thereafter, casting (Nunc™ Cell-Culture Treated Multidishes 24-well plates) and freeze-drying were performed to obtain the biomaterial of the present invention (a solid after drying, and also in a solid form in use), and a microstructure diagram thereof is shown in FIG. 1. The small white dot in FIG. 1 (see white arrows) is the hypoglycemic drug. The two diagrams above and below show different magnifications (the upper is 200× magnification; the lower is 3500× magnification). The upper diagram shows that the pore size is suitable for bone growth, and the lower diagram shows the coating of the hypoglycemic drug. In this example, the enzyme cross-linking agent is a binder, which is crosslinked by an enzyme selected from the group consisting of: transglutaminase, lipase, peptidase, sortase, oxidoreductase, tyrosinase, polyphenoloxidase (PPO), laccase, peroxidase, lysyl oxidase, and amine oxidase.

Mesenchymal stem cells (MSCs) can differentiate into osseous bone, cartilage, adipose and other connective tissues or transdifferentiate into neural cells, liver cells, etc., which are called monoblastic pluripotent stem cells.

Subsequently, mesenchymal stromal cells (MSCs) obtained from patients who need to promote bone regeneration (IRB number 201904070RINA) were cultured, and a control group and an experimental group of cells were prepared. 5% (v/v) biomaterial in the form of MGS microsphere was added to the cells in the experimental group, while the cells in the control group were not added with the biomaterial. After 3, 7, 14, 21, or 28 days of treating the cells, the cell culture was collected and used for gene expression analysis.

In this example, the osteoblast-specific genes used for analysis include alkaline phosphatase (ALPP) gene, runt-related transcription factor 2 (RUNX2) gene, osterix (SP7) gene, osteonectin (SPARC) gene, osteocalcin (BGLAP) gene, and collagen type I alpha 1 (COL1A1) gene.

RNA extraction was performed on the cell culture obtained above using Qiazol (Qiagen, Valencia, Calif.), and random hexamers (Vivantis Inc., California) and reverse transcriptase (Vivantis Cat No: RTPL12) were used to reverse-transcribe the extracted RNA into cDNA. The cDNA was used as a template, primer pairs for amplification of target genes, including ALPP, RUNX2, SP7, SPARC, BGLAP, COL1A, and GAPDH (as an endogenous control group) were used for osteogenic differentiation, and their nucleotide sequences are shown in Table 1. TOOLS 2X SYBR qPCR Mix (Biotools Co., Ltd., Taipei, Taiwan) was applied for real-time RT-PCR using CFX Connect Real-Time PCR Detection System (BioRed, CA, USA) to amplify the target genes.

TABLE 1

| Target gene | SEQ ID NO. | #Primer name | Sequence (5' --> 3') |
| --- | --- | --- | --- |
| ALPP | 1 | ALPP-F | GAGAAGCCGGGACACAGTTC |
|  | 2 | ALPP-R | CCTCCTCAACTGGGATGATGC |
| RUNX2 | 3 | RUNX2-F | TAGGCGCATTTCAGGTGCTT |
|  | 4 | RUNX2-R | GGTGTGGTAGTGAGTGGTGG |
| SP7 | 5 | SP7-F | TAGGACTGTAGGACCGGAGC |
|  | 6 | SP7-R | CATAGTGAACTTCCTCCTGGGG |
| SPARC | 7 | SPARC-F | ATTGACGGGTACCTCTCCCA |
|  | 8 | SPARC-R | GAAAAAGCGGGTGGTGCAAT |
| BGLAP | 9 | BGLAP-F | CTCACACTCCTCGCCCTATTG |
|  | 10 | BGLAP-R | GCTTGGACACAAAGGCTGCAC |
| COL1A1 | 11 | COL1A1-F | AGAGGTCGCCCTGGAGC |
|  | 12 | COL1A1-R | CAGGAACACCCTGTTCACCA |
| GAPDH | 13 | GAPDH-F | AATGGGCAGCCGTTAGGAAA |
|  | 14 | GAPDH-R | GCCCAATACGACCAAATCAGAG |

PCR parameters were as follows: 95° C. for denaturation (3 min), 40 cycles of 95° C. for 20 s, 60° C. for annealing (30 s), and 72° C. for elongation (30 s). The expression of the target genes was calculated in using glyceraldehyde 3-phosphate dehydrogenase (GAPDH) as an endogenous control, wherein $\Delta Ct=Ct_{target\ gene}-Ct_{GAPDH}$, $\Delta\Delta Ct = \Delta Ct_{test\ sample}-\Delta Ct_{control\ sample}$, fold change=$2^{-\Delta\Delta Ct}$. The control group was internalized (normalized). The control group was made as 1 fold, and the fold change of the experimental group was calculated compared to that of the control group. There is no control group in the presentation of the diagram, only the expression of the experimental group, because the fold of the control group is 1. The results of this example are shown in FIG. 2.

Figure 2:
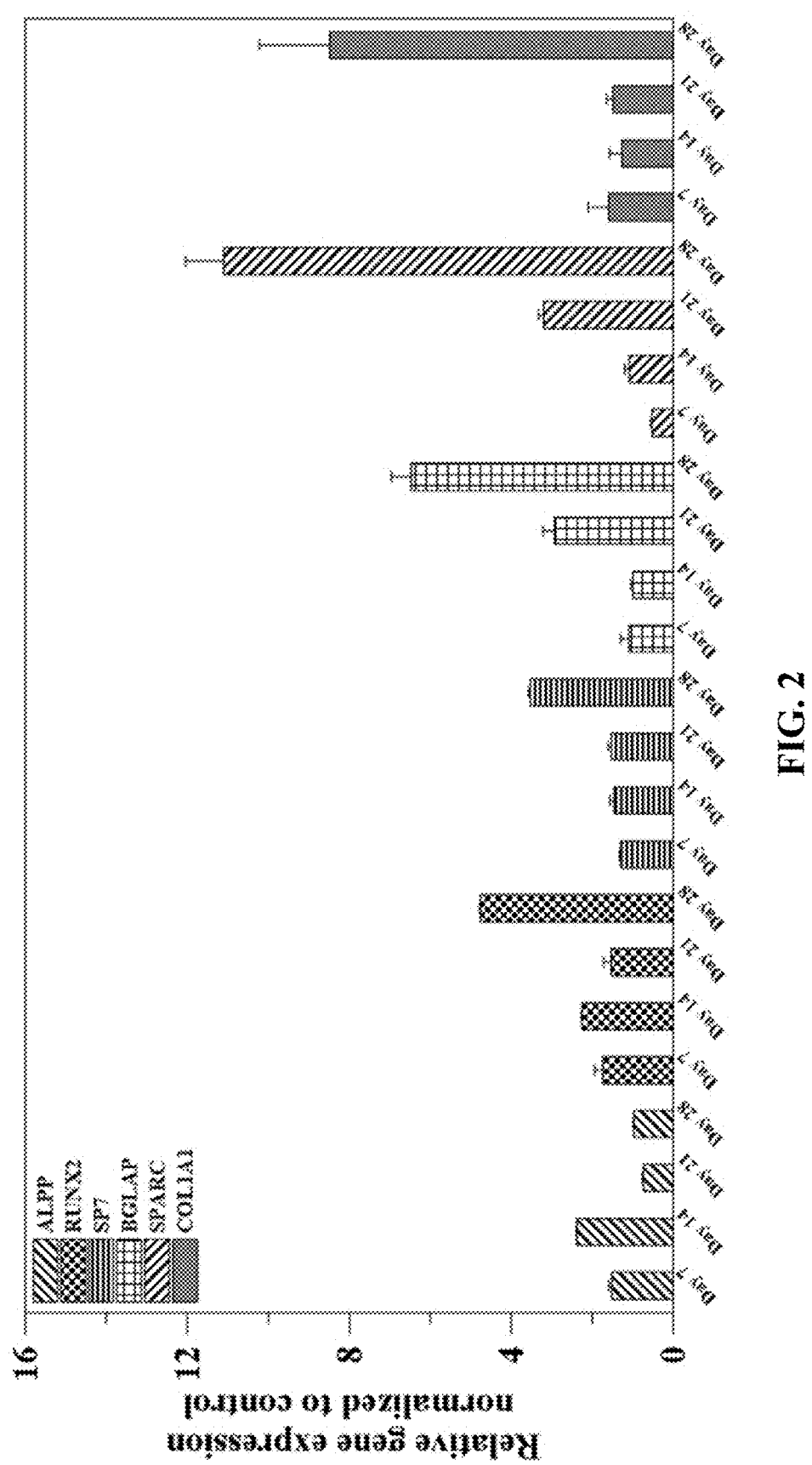
FIG. 2 is a data diagram showing the effect of the biomaterial of the present invention (using insulin as a hypoglycemic drug component) on regulating osteoblast-specific genes on the 7th, 14th, 21th, and 28th days after treating cells.

FIG. 2 is a data diagram showing the effect of the biomaterial of the present invention (using insulin as a hypoglycemic drug component) on regulating osteoblast-specific genes on the 7th, 14th, 21th, and 28th days after treating cells. As shown in FIG. 2, after normalization in the control group, the expression levels of osteoblast-specific genes (including ALPP, RUNX2, SP7, SPARC, BGLAP and COL1A1 genes) were upregulated on the 7th, 14th, 21th, and 28th days after the mesenchymal stem cells (MSCs) were treated with the biomaterial of the present invention (using insulin as a hypoglycemic drug component).

Example 2

Evaluation of Effect of Biomaterial on Promoting Regeneration of Bone Tissues

The surgical procedures were standardized for the creation of in vivo bone defect sites in the rat model. For the in vivo surgical analysis, a total of 27 rats (6-week-old male rats) were obtained from the Center for Laboratory Animals, College of Medicine, National Taiwan University and anesthetized with a 1:2 concentration of Zoletil and Rompum (1 mL/kg) via intraperitoneal injection. A single bone defect was created at the ulna in an aseptic surgical environment. A bone defect of 5 mm was generated from the middle of ulna (this is a bone defect that is more severe than general bone defects). The bone defects were then filled with the biomaterial of the present invention (using metformin as a hypoglycemic drug component). A bone defect without any filling material as a control. After the implantation of the bone graft, the wound closure was performed using 5-0 absorbable sutures. A computed tomography (CT) scan was performed 4 weeks after implantation of the bone graft, and the experimental result is shown in FIG. 3.

Figure 3:
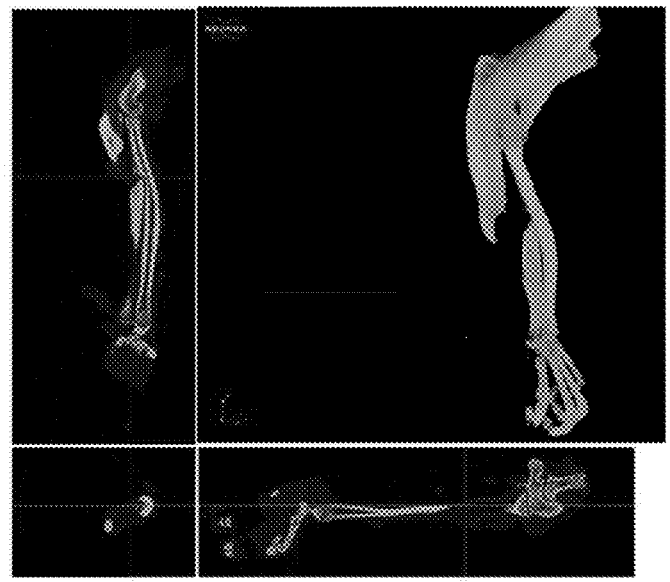
FIG. 3 is a computed tomography diagram showing the effect of the biomaterial of the present invention on promoting regeneration of bone tissues.
Figure 3:
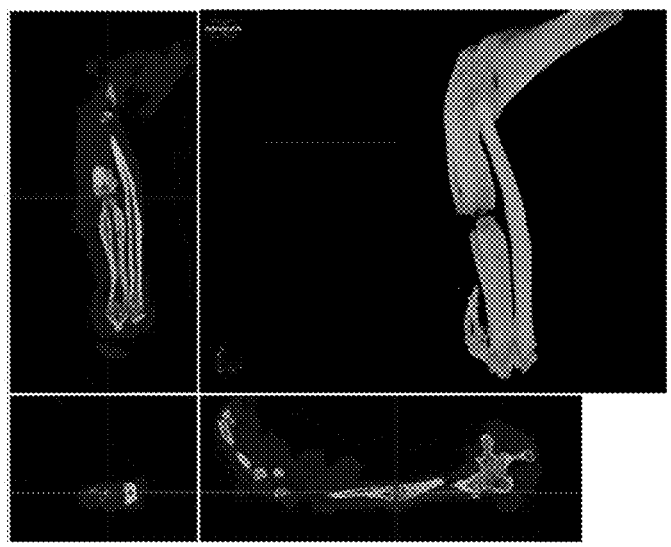

FIG. 3 is a computed tomography diagram showing the effect of the biomaterial of the present invention on promoting regeneration of bone tissues. As shown in FIG. 3, compared with the control group (upper), the experimental group (lower) using the biomaterial of the present invention (with metformin as a hypoglycemic drug component) as the bone filling can significantly promote regeneration of bone tissues.

In summary, the biomaterial of the present invention has the effect on regulating osteoblast-specific genes (including alkaline phosphatase (ALPP) gene, runt-related transcription factor 2 (RUNX2) gene, osterix (SP7) gene, osteonectin (SPARC) gene, osteocalcin (BGLAP) gene, and collagen type I alpha 1 (COL1A1) gene) to promote tissue regeneration (such as regeneration of bone tissues), and human experiments are also proved effective.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A biomaterial for promoting regeneration of bone tissues, consisting of a biocompatible polymer, an inorganic salt, a cross-linking agent, and a hypoglycemic drug;
   wherein the inorganic salt is dicalcium phosphate (DCP) or dicalcium phosphate dihydrate (DCPD);
   wherein the biocompatible polymer is in a form of a sphere or a film;
   wherein the cross-linking agent is selected from the group consisting of lipase, peptidase, sortase, oxidoreductase, polyphenoloxidase (PPO), lysyl oxidase, and amine oxidase;
   wherein promotion of regeneration of bone tissues is essentially from the hypoglycemic drug;
   wherein the biocompatible polymer is alginate.

2. The biomaterial according to claim 1, wherein the hypoglycemic drug is selected from the group consisting of biguanide, insulin, sulfonylurea, meglitinide, thiazolidinedione, an α-glucosidase inhibitor, a dipeptidyl peptidase 4 (DPP-4) inhibitor, a sodium-glucose transport protein 2 (SGLT2) inhibitor, and bromocriptine.

3. The biomaterial according to claim 2, wherein the biguanide is metformin.

4. The biomaterial according to claim 2, wherein the Sulfonylurea is selected from the group consisting of glipizide, glyburide, gliclazide, and glimepiride.

5. The biomaterial according to claim 2, wherein the meglitinide is a repaglinide or a nateglinide.

6. The biomaterial according to claim 2, wherein the thiazolidinedione is a rosiglitazone or a pioglitazone.

7. The biomaterial according to claim 2, wherein the α-Glucosidase inhibitor is selected from the group consisting of acarbose, miglitol, and voglibose.

8. The biomaterial according to claim 2, wherein the DPP-4 inhibitor is selected from the group consisting of sitagliptin, saxagliptin, vildagliptin, linagliptin, and alogliptin.

9. The biomaterial according to claim 2, wherein the SGLT2 inhibitor is a dapagliflozin or a canagliflozin.

10. The biomaterial according to claim 1, wherein the biocompatible polymer has a concentration of 1-50% (w/v), the inorganic salt has a concentration of 1-50% (w/v), the hypoglycemic drug has a concentration of 1 nM-1 M, and the cross-linking agent has a concentration of 1-50 wt %.

11. The biomaterial according to claim 1, wherein the biocompatible polymer or the inorganic salt has an average size from 1 nm to 1 mm.

12. A method for promoting tissue regeneration, comprising administering to a subject in need thereof the biomaterial according to claim 1.

13. The method according to claim 12, wherein the biocompatible polymer has a concentration of 1-50% (w/v), the inorganic salt has a concentration of 1-50% (w/v), the hypoglycemic drug has a concentration of 1 nM-1 M, and the cross-linking agent has a concentration of 1-50 wt %.

* * * * *